United States Patent [19]

Bianco et al.

[11] Patent Number: 4,985,632

[45] Date of Patent: Jan. 15, 1991

[54] SUNTAN INDICATOR

[75] Inventors: Frank J. Bianco, Pembroke Pines; Charles W. Owen; Elie Talamas, Jr., both of Miami, all of Fla.

[73] Assignee: Elexis Corporation, Miami, Fla.

[21] Appl. No.: 359,680

[22] Filed: May 31, 1989

[51] Int. Cl.⁵ .............................................. G01J 1/42
[52] U.S. Cl. .................................................. 250/372
[58] Field of Search ........................................ 250/372

[56] References Cited

U.S. PATENT DOCUMENTS

| | | | |
|---|---|---|---|
| 3,710,115 | 1/1973 | Jubb | 250/372 |
| 3,851,970 | 12/1974 | Adler et al. | 356/51 |
| 3,891,849 | 6/1975 | Felice et al. | 250/372 |
| 3,917,948 | 11/1975 | Strutz | 250/372 |
| 3,971,943 | 7/1976 | Jeunehomme et al. | 250/372 |
| 4,010,372 | 3/1977 | Adler et al. | 250/372 |
| 4,015,130 | 3/1977 | Landry et al. | 250/372 |
| 4,065,672 | 12/1977 | Harpster | 250/372 |
| 4,086,489 | 4/1978 | Piltingsrud | 250/372 |
| 4,229,733 | 10/1980 | Tulenko et al. | 340/500 |
| 4,348,664 | 9/1982 | Boschetti et al. | 340/600 |
| 4,428,050 | 1/1984 | Pellegrino et al. | 364/414 |
| 4,485,306 | 11/1984 | Braunstein et al. | 250/372 |
| 4,535,244 | 8/1985 | Burnham | 250/372 |
| 4,608,492 | 8/1986 | Burnham | 250/372 |
| 4,608,655 | 8/1986 | Wolf et al. | 364/569 |
| 4,704,535 | 11/1987 | Leber et al. | 250/372 |
| 4,825,078 | 4/1989 | Huber et al. | 250/372 |
| 4,851,685 | 7/1989 | Dübgen | 250/372 |
| 4,851,686 | 7/1989 | Pearson | 250/372 |

FOREIGN PATENT DOCUMENTS 2181833A 4/1987 United Kingdom .

OTHER PUBLICATIONS

Berger, *Photochemistry & Photobiology*, 1976, vol. XXIV, pp. 587-593.

Primary Examiner—Constantine Hannaher
Assistant Examiner—Edward J. Glick
Attorney, Agent, or Firm—Lowe, Price, LeBlanc, Becker & Shur

[57] ABSTRACT

An electronic wristwatch having an LCD for time of day, day of month and month of year, as well as four key switches, includes a photodiode for detecting skin damaging ultraviolet, tanning radiation. The photodiode, a microcomputer, key switches, display and a battery are electrically connected to each other so that in response to activation of the key switches the microcomputer stores signals indicative of the time functions, intensity of the skin damaging ultraviolet radiation instantaneously incident on the photodiode at the time one of the key switches is activated, skin type of a subject wearing the watch, subject sun protection factor, and elapsed time from the time one of the key switches is activated, and the remaining time the subject skin can be safely exposed to the skin damaging radiation. The remaining time indication is derived independently of accumulated radiation incident on the photodiode which need not be pointed at the radiation source except when the one key is activated. The remaining time indication can be modified by subsequently pointing the detector at the radiation source and/or entering a different sun protection factor.

17 Claims, 6 Drawing Sheets

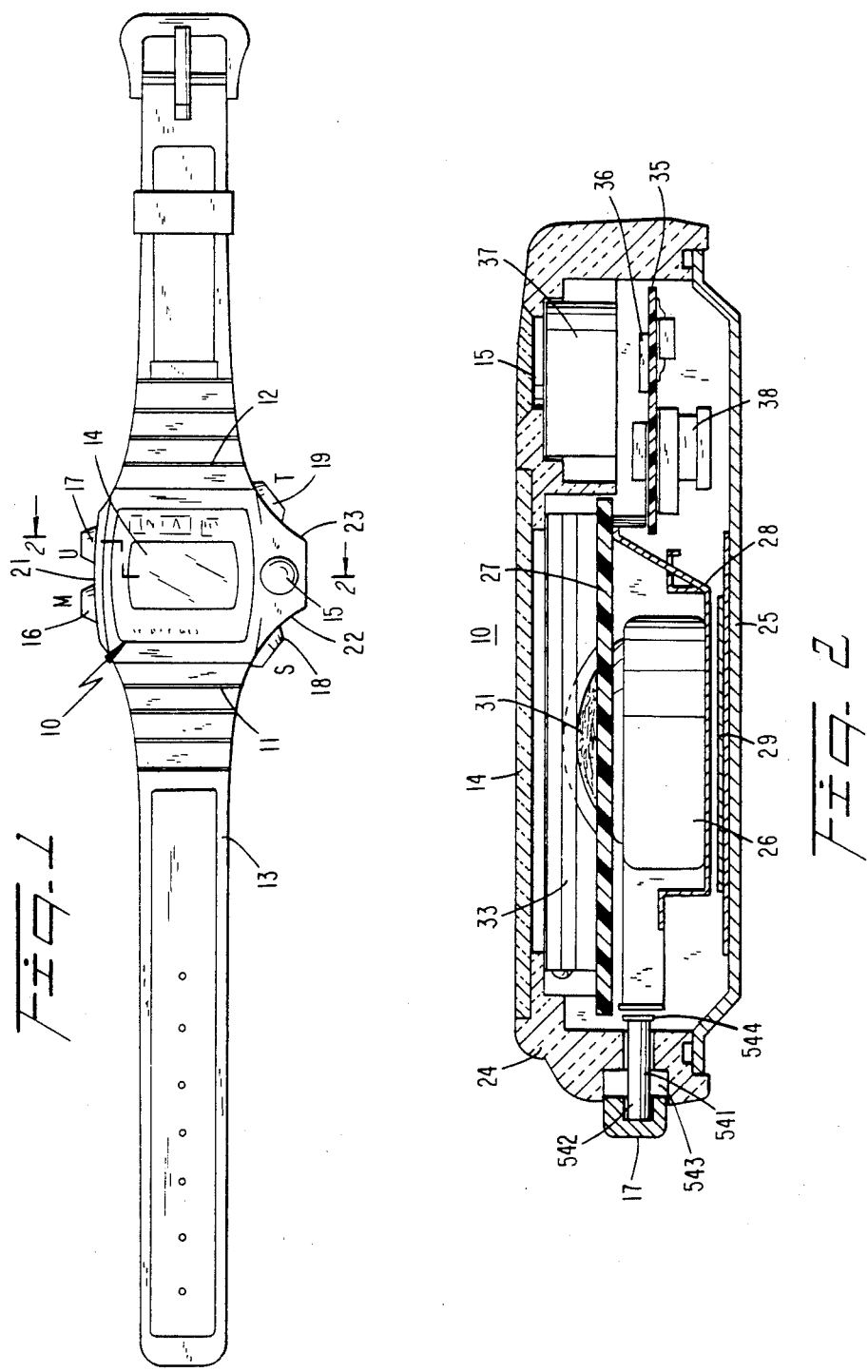

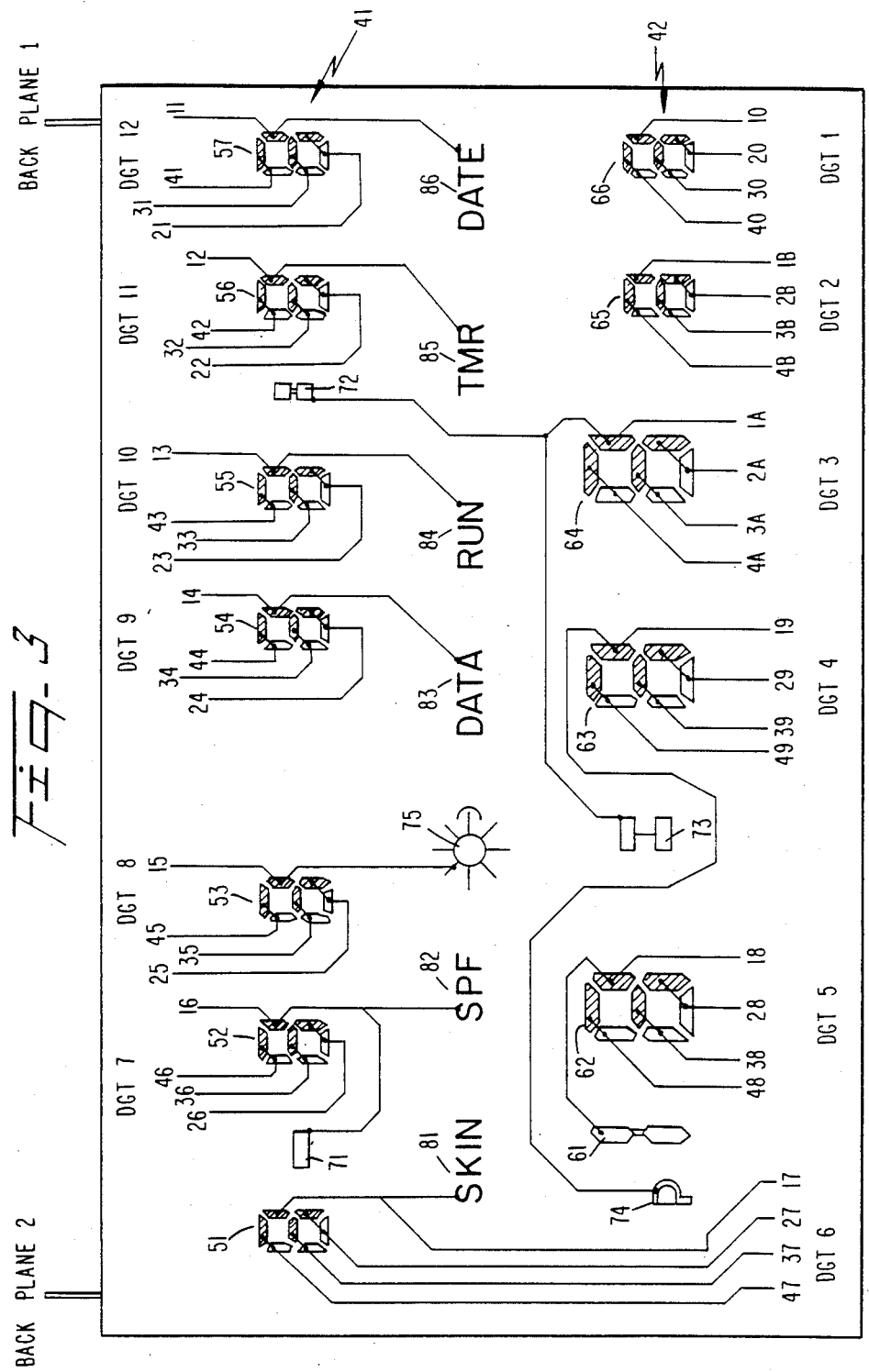

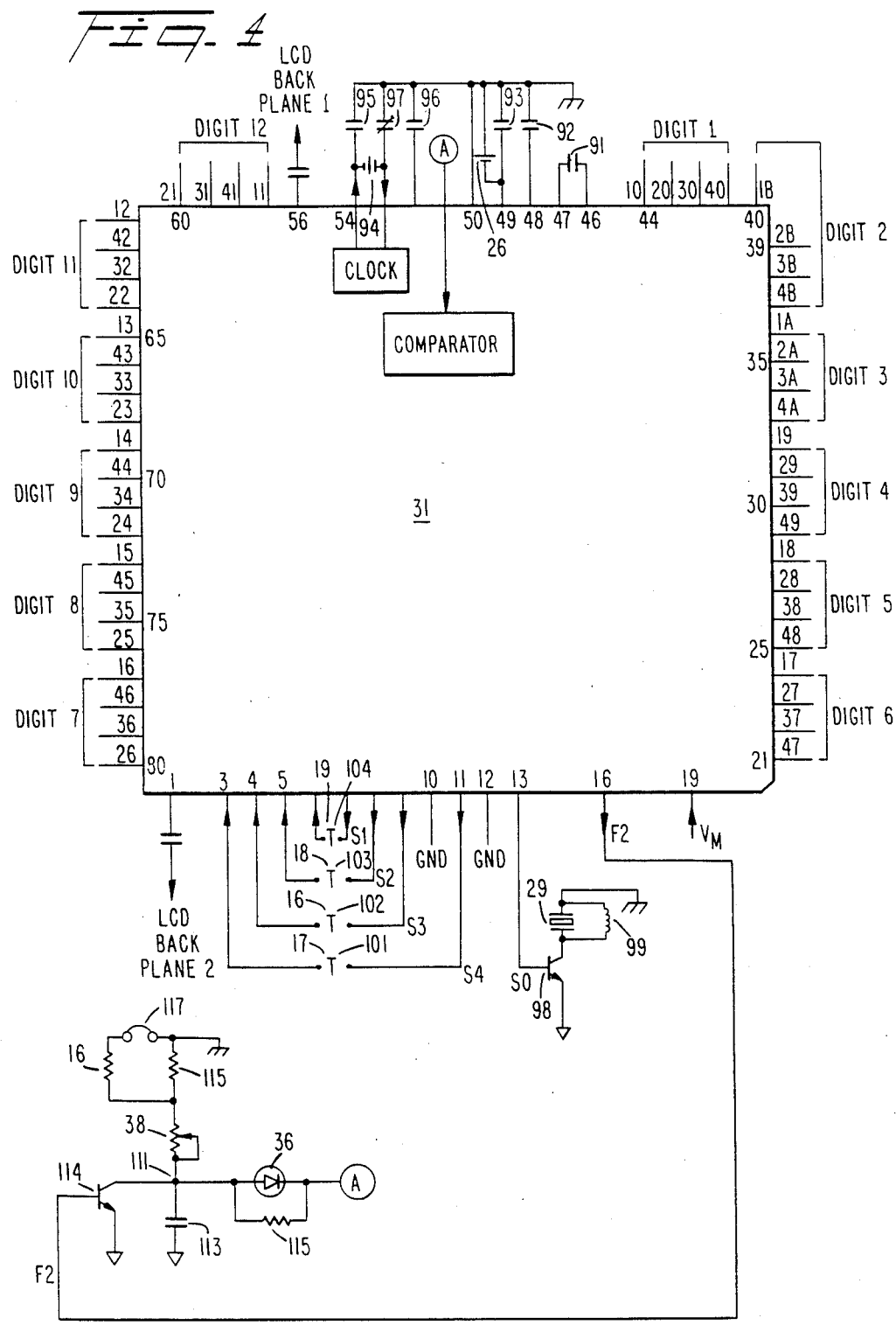

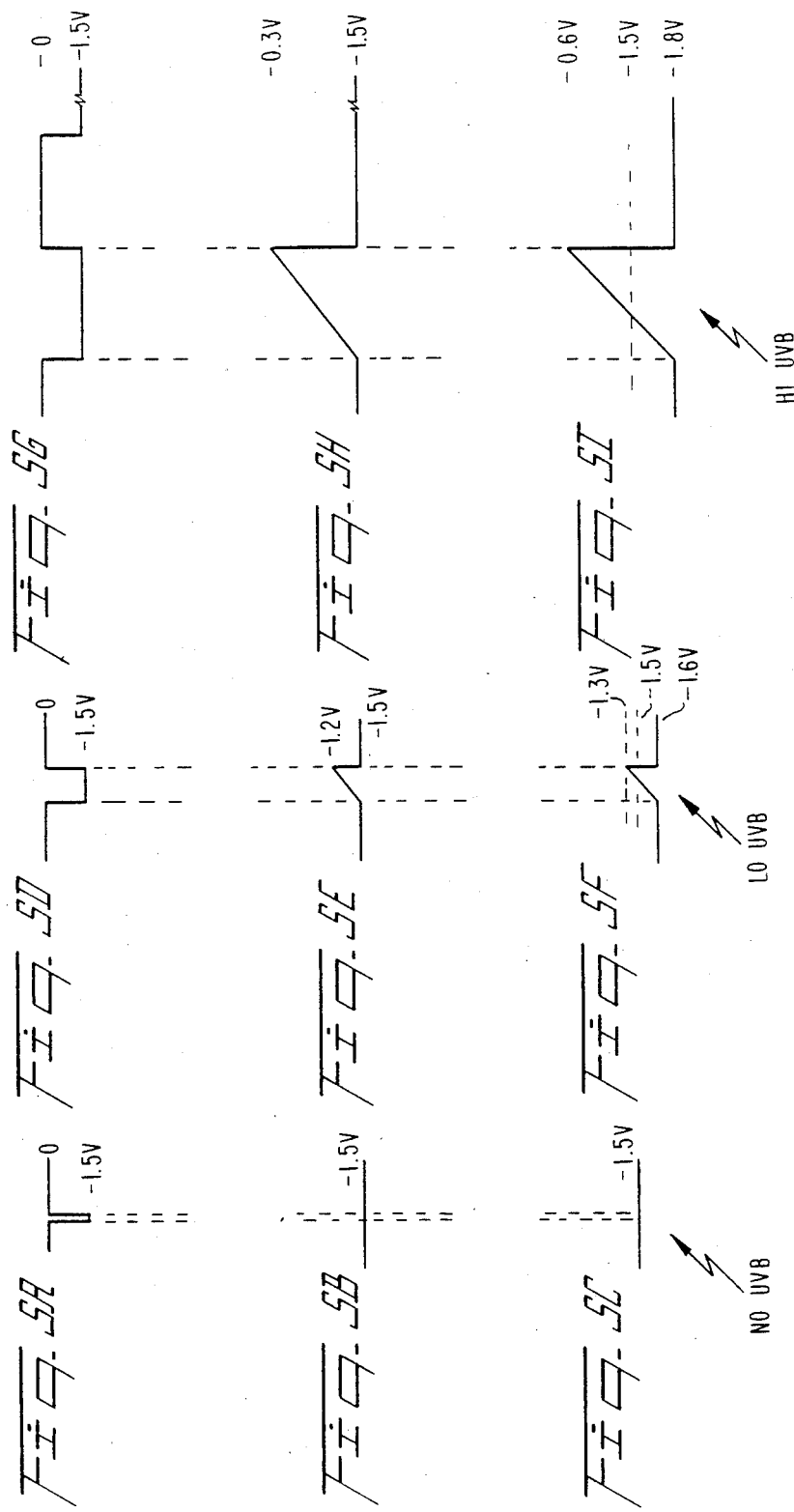

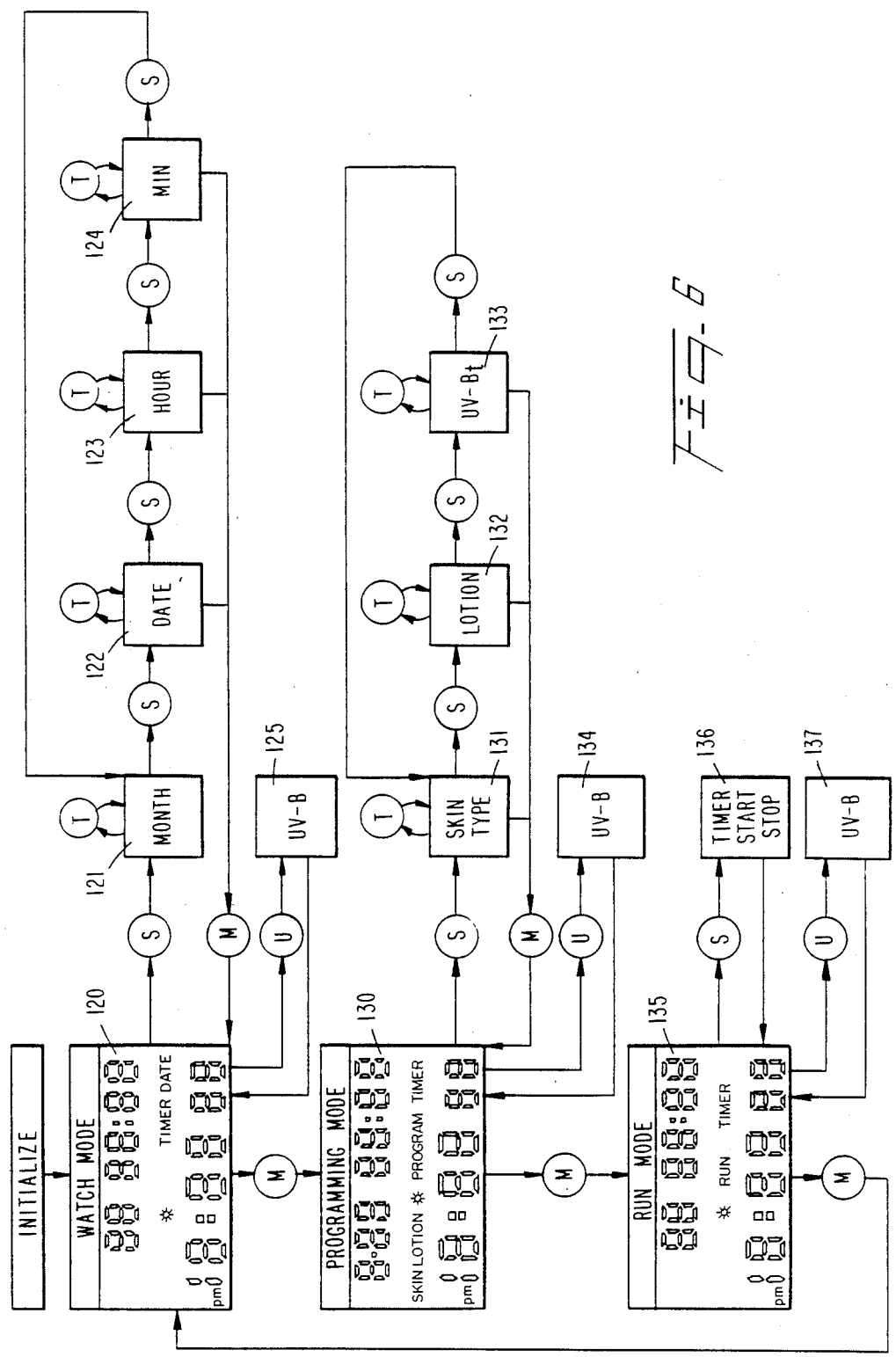

SUNTAN INDICATOR

FIELD OF INVENTION

The present invention relates generally to signalling for skin damaging ultraviolet radiation and more particularly to a signalling method and apparatus wherein an indication is derived for the remaining time skin of a subject can be safely exposed to skin damaging ultraviolet radiation independently of accumulated radiation incident on a photodetector for the radiation.

BACKGROUND ART

Several devices have been proposed and at least two marketed to determine when excessive skin damaging ultraviolet B (UVB) radiation is incident on a subject. The devices are usually used to enable a subject to be apprised of excessive sun exposure during suntanning sessions or the like.

The prior art devices have generally included a UVB radiation photodetector which drives electronic circuitry. The circuitry responds to accumulated radiation incident on the detector during an exposure session. The circuitry may also be responsive to signals indicative of subject skin type and sun protection factor (SPF) of the skin. The sun protection factor is determined by UVB blocking materials, either a lotion or gel, applied to the subject's skin. If no sun protecting lotion or gel is applied to the subject's skin, the sun protection factor is one. As the blocking capability of the lotion or gel increases, the sun protection factor associated therewith increases accordingly. Typically, the skin type and sun protection factor indications are combined to derive an indication of the length of time the subject can be exposed to the skin damaging UVB radiation. In response to the accumulated skin damaging UVB radiation incident on the subject reaching a preset value determined by SPF and skin type, an indicator, which may be aural and/or visual, is activated.

The prior art devices have either been laboratory devices, not suitable for commercialization because of size and cost constraints and because of difficulty in use, or relatively expensive commercial devices. Neither attempt to commercialize has apparently been particularly successful.

The prior art devices have required the user to place the device in close proximity to his location at a position where the photodetector is constantly exposed to the source of skin damaging UVB radiation in the same manner that the skin is exposed to the UVB source. Such positioning is necessary to enable the accumulated skin damaging UVB radiation incident on the detector, and therefore on the subject, to be accumulated. Such placement of the device has obvious disadvantages, relating, for example, to the likelihood of losing the device, sand or dirt blocking the detector field of view, sand or dirt penetrating the interior of a case for the device, and mounting the device so that the intensity of the skin damaging UVB radiation incident on the photodetector is approximately the same as the intensity of the radiation incident on the subject's skin.

Some of these problems can be resolved if the detector and circuitry associated therewith are in a housing easily mounted on the body of the subject. Such a housing would conveniently be in the form of a wristwatch. A problem, however, in mounting the prior art devices on the body of the subject is that the detector for the skin damaging ultraviolet radiation is not exposed to the radiation source in the same manner that much of the skin of the subject is exposed to the radiation. Hence, the accumulated radiation on the detector is likely to be a very inaccurate indicator of the actual amount of radiation experience by the subject.

A further problem, from a commercial standpoint, in mounting an indicator for exposure time to skin damaging UVB radiation in a watch casing is that the consumer expects the cost of such an indicator to be about the same as for a sports electronic wristwatch or timepiece. Hence, the number of parts which can be added to a conventional sports, electronic wristwatch or timepiece to provide the exposure time indicator function must be minimized. Otherwise, the cost of the device will be such that there is a low likelihood of consumer acceptance. Preferably, the elapsed time indicator for skin damaging UVB radiation is combined with watch functions of a modern electronic watch, i.e., time of day, day of the month and month of the year.

It is, accordingly, an object of the present invention to provide a new and improved apparatus for and method of indicating the expiration of maximum safe elapsed exposure time of skin of a subject to damaging ultraviolet radiation.

Another object of the present invention is to provide a new and improved apparatus for and method of indicating when maximum safe elapsed exposure time to skin damaging ultraviolet radiation has expired independently of radiation accumulated on a detector for such radiation.

A further object of the present invention is to provide a device adapted to be worn on a subject, to signal to the subject that maximum safe exposure time to skin damaging ultraviolet radiation has expired, even though a detector in the device is not constantly pointed at a source of the radiation.

An additional object of the present invention is to provide a new and improved device mounted in a wristwatch type casing for indicating to a subject that maximum safe exposure time of the skin of the subject to skin damaging ultraviolet radiation has expired.

An additional object of the present invention is to provide a new and improved device that has approximately the same cost as an electronic sports wristwatch, and which provides many of the functions of an electronic sports wristwatch as well as indications of the expiration of maximum safe exposure time of skin of a subject wearing the device to skin damaging ultraviolet radiation.

An additional object of the invention is to provide a new and improved device including a detector responsive to skin damaging ultraviolet radiation connected by a minimum number of parts to a microcomputer which drives an LCD display, wherein the entire device has a cost approximating that of a conventional electronic sports watch.

Another object of the invention is to provide a new and improved apparatus for and method of indicating maximum safe elapsed exposure time of a subject to skin damaging ultraviolet radiation wherein variations in radiation intensity, sun protection factor and interruptions in exposure are accommodated.

DISCLOSURE OF THE INVENTION

In accordance with one aspect of the invention, the maximum amount of time skin of a subject can be safely exposed to skin damaging ultraviolet radiation is determined with a detector for the radiation and in response to indications of subject skin type and sun protection factor of the subject skin. In response to the indications and an instantaneous value of said radiation incident on the detector, the maximum length of time the subject can be safely exposed to the radiation is initially calculated, preferably by a computer. A clock or other type of timer is activated in response to the instantaneous value being detected. An indication of when the amount of time the subject can be safely exposed to the radiation has expired is derived in response to the time indication and the initially calculated time, independently of the accumulated radiation incident on the detector. Thereby, the detector need not be constantly exposed to the skin damaging ultraviolet B radiation. Because the detector need not be constantly exposed to the radiation, the device can be worn on the subject at a convenient location, such as by being mounted in a wristwatch that is worn in the usual place on the subject.

An important feature of the invention is that the calculated length of time the subject can be safely exposed to the radiation can be modified in response to an instantaneous value of the radiation incident on the detector at a time subsequent to the time when the detector was previously responsive to the radiation and/or when the sun protection factor for the subject skin changes. Thereby, if the subject is of the opinion that the intensity of the skin damaging ultraviolet B radiation source has changed after initial exposure of the detector to the source, a second reading is taken and/or a lotion having a different SPF is applied. The instantaneous level of the radiation at the time of the second reading and/or the different SPF modifies the previously calculated exposure time.

In accordance with a further aspect of the invention, a combined timepiece and UVB indicator device includes a case having a fastener, such as a wristwatch strap, for enabling the case to be fixed to a human subject. The case includes a microcomputer, a digital indicator, plural key switches, a battery, a window and a photodetector behind the window. The window and photodetector have optical characteristics such that the photodetector derives a response indicative of skin damaging ultraviolet radiation incident on a subject wearing the device. The microcomputer includes an oscillator and registers. The photodetector, microcomputer, key switches, indicator (preferably a digital LCD) and battery are electrically connected to each other so that in response to activation of the key switches the register stores signals indicative of time of day, intensity of skin damaging ultraviolet radiation instantaneously incident on the photodetector, subject skin type, subject sun protection factor and elapsed time from the time the photodetector was initially exposed to the radiation. The registers are connected to the indicator so that the indicator displays digits indicative of time of day, the intensity of the skin damaging ultraviolet radiation instantaneously incident on the photodetector at the time the photodetector was exposed, subject skin type, subject sun protection factor and the remaining time the subject skin can be safely exposed to the skin damaging radiation from the time one of the key switches is activated independently of accumulated radiation incident on the photodetector. The indicator can also be an aural indicator, such as a beeper included in modern electronic timepieces.

To enable the price of the combined suntan indicator and timepiece to be approximately the same as modern electronic sports wristwatches, the additional component count relative to that of such a wristwatch is minimized. The microcomputer is a CMOS (i.e., complementary metal oxide semiconductor) structure having a pair of DC power supply terminals connected to a battery. The CMOS structure includes a comparator which derives an output signal having first and second values in response to the voltage at a signal input terminal thereof having values on first and second opposite sides of a reference voltage of the comparator. The photodetector, which is a photovoltaic generator, is connected between the signal input terminal and a connection between a switch, preferably the emitter collector path of a single bipolar transistor, and a capacitor. The switch and capacitor are connected to the DC power supply terminals so that when the switch is closed both electrodes of the capacitor are substantially at the voltage of one of the supply terminals and when the switch is open the capacitor is charged primarily by current generated by the photodetector. Because of the photovoltaic nature of the photodetector and these connections, the voltage at the comparator signal input terminal is frequently beyond the voltage at the DC power supply terminals while the switch is closed.

The switch is controlled in response to the levels derived by the comparator to cause the switch to be open and closed while the comparator is respectively deriving the first and second levels. The comparator derives the first level for an interval that increases as the magnitude of the voltage of the element increases. The microcomputer converts the interval during which the first level is derived into a digital signal having a value indicative of the length of the first interval and therefore of the UVB intensity.

The total component count needed to obtain the indication of UVB radiation incident on the detector is increased by only a single transistor, a single capacitor, the photodiode and associated optical filter, three resistors, and a factory set variable resistor. Thereby, the price of components and installation thereof is minimized so that the price of the device to the consumer is approximately the same as that of a conventional multifunction sports watch.

The above and still further objects, features and advantages of the present invention will become apparent upon consideration of the following detailed description of a specific embodiment thereof, especially when taken in conjunction with the accompanying drawings.

BRIEF DESCRIPTION OF DRAWINGS

FIG. 1 is a top view of an electronic timepiece combined with an indicator for skin damaging ultraviolet B radiation in accordance with a preferred embodiment of the invention;

FIG. 2 is a sectional view through the lines 2—2, FIG. 1;

FIG. 3 is a top view of a liquid crystal display (LCD) utilized in the watch of FIGS. 1 and 2;

FIG. 4 is a circuit diagram of electronic components utilized in the watch illustrated in FIGS. 1-3;

FIGS. 5a-5i are a series of waveforms helpful in describing the operation of a portion of the circuit illustrated in FIG. 4;

FIG. 6 is a flow diagram of operations performed by a user of the device illustrated in FIGS. 1-4.

DESCRIPTION OF THE PREFERRED EMBODIMENT

Figure 7:
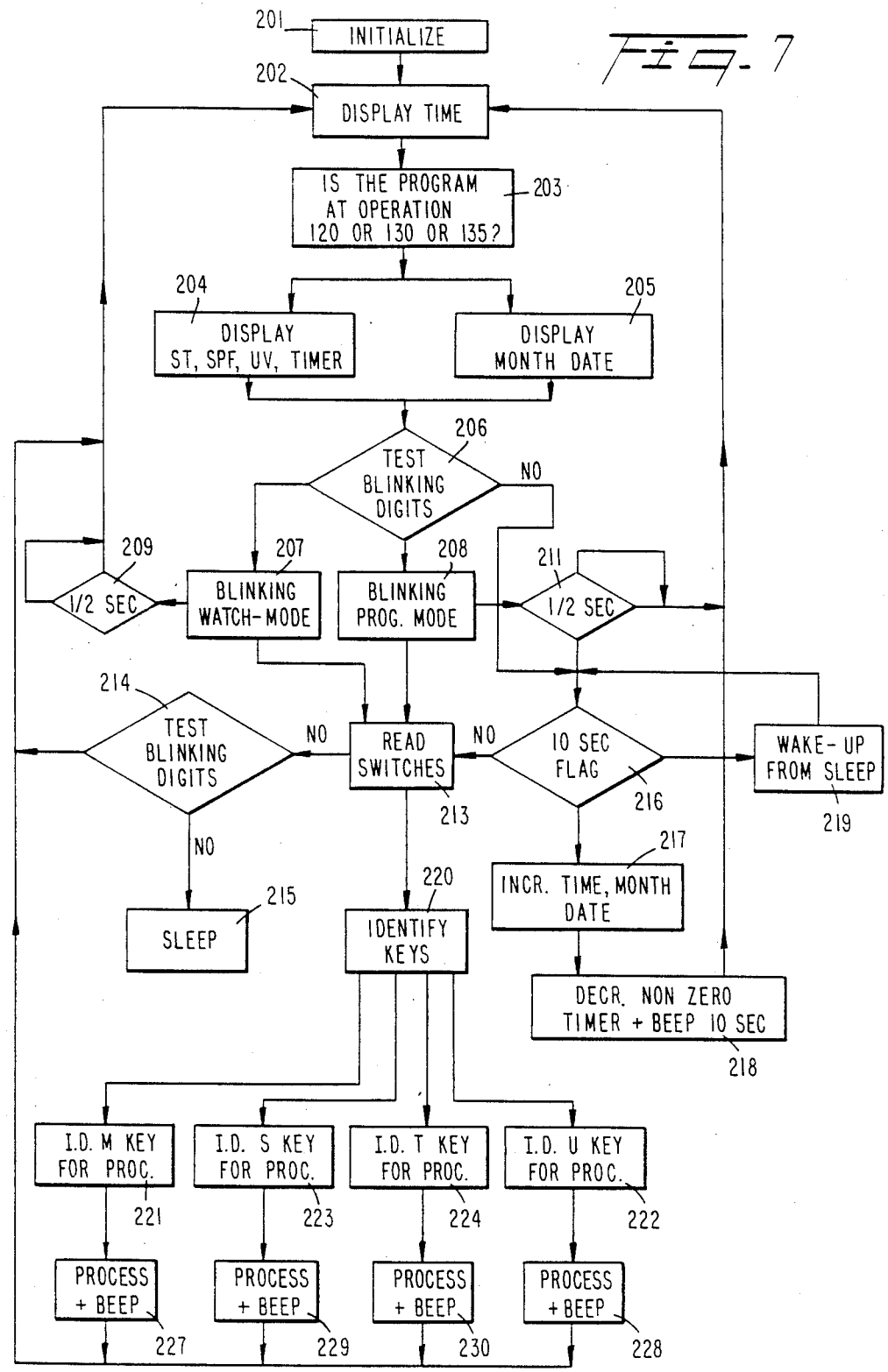
FIG. 7 is a flow diagram of operations performed by a microcomputer included in the device illustrated in FIGS. 1-4.

Reference is now made to FIG. 1 of the drawing wherein there is illustrated a combined electronic timepiece and detector-indicator for skin damaging UVB radiation. The device illustrated in FIG. 1 is configured as a wristwatch including watch case 10, having opposite edges 11 and 12 to which are affixed wristwatch strap 13. On the upper face of watch case 10 is lens or crystal 14 behind which is located a multicharacter liquid crystal display. To one side of lens 14, between edges 11 and 12, is window 15 behind which are a filter for passing UVB and a photodetector, of the photovoltaic type.

Pushbuttons or keys 16-19 are mounted on side walls of case 10 between edges 11 and 12. Pushbuttons 16-19, in combination with electric contacts controlled by the buttons, effectively function as key switches for controlling time settings of the liquid crystal display, entry of data concerned with skin type of a subject wearing the device illustrated in FIG. 1, sun protection factor of the skin of the subject. The amount of ultraviolet B radiation incident on the skin of the subject is determined when a button is pressed while window 15 is pointing at the UVB source. In particular, M button 16 (mode button) and U button 17 (UVB sensor button) extend from convex side wall 21 that extends continuously between edges 11 and 12, while S button 18 (advance button) and T button 19 (digital data entry) extend from concave side wall segments 22 and 23, located in proximity to window 15.

As illustrated in FIG. 2, lens 14 and glass window 15 are fixedly mounted in roof 24 of watch case 10, having a removable metal back plate 25 for enabling insertion and removal of one 1.5 volt silver oxide battery cell 26. Opposite polarity electrodes of battery 26, on opposite faces of the battery, are electrically connected to a contact on printed circuit board 27 and battery plate 28, against which the electrodes abut. Battery 26 is thereby loaded into a compartment between printed circuit board 27 and battery plate 28 in such a manner that the electrodes of the battery, on opposite faces thereof, are parallel to parallel planes in which back plate 25 and lens 14 are located.

Back plate 25 carries piezoelectric crystal 29 which produces aural beeps in response to signals derived from CMOS (complementary metal oxide semiconductor) microcomputer 31, mounted on a face of printed circuit board 27 opposite from the face of the printed circuit board having a contact (not shown) that engages an electrode of battery 26. Microcomputer 31 and other components in case 10 are supplied with electric current by battery 26, by virtue of the opposite polarity electrodes of the battery engaging printed circuit board 27 and battery plate 28 that is connected to the printed circuit board. In the preferred embodiment, microcomputer 31 is a SHARP SM530 4-bit microprocessor.

Liquid crystal display 33, located between lens 14 and printed circuit board 27, is disposed so that the numeric bearing face thereof is parallel to the lens and printed circuit board, in a position facing toward the lens. Display 33 includes numerous input terminals connected to output terminals of microcomputer 31. Microcomputer 31 drives numeric indicating elements of liquid crystal display 33 to display time of day, to the nearest second, day of the month, month of the year, subject skin type, sun protection factor and radiation intensity of the most recent reading of the UVB detector. In addition, the liquid crystal display provides a user of the watch with an indication of the amount of residual time he may safely be exposed to the UVB radiation source and the initial reading of the detector. The display is controlled in response to activation of the key switches associated with pushbuttons 16-19, as well as in response to the intensity of the radiation incident on UVB photodetector 36 included in case 10.

UVB detector 36 is mounted on a second, smaller printed circuit board 35, positioned in case 10 behind window 15. Printed circuit board 35 and detector 36 are disposed in case 10 so they lie in planes parallel to lens 14 and back plate 25. Positioned between the upper, detecting face of photodetector 36 and window 15 is filter 37 which passes UVB, to the substantial exclusion of virtually all other optical radiation, to which detector 36 is otherwise responsive. In the preferred embodiment, filter 37 has a peak transmissivity at 303.4 nanometers, with cutoffs at 377.4 and 266.6 nanometers. At the high and low wavelength cutoffs, the filter transmissivities are respectively 0.40 percent and 0.32 percent; at maximum transmissivity, filter transmissivity is 58.45 percent. Photodetector 36, being a photodiode of the photovoltaic type, generates a DC voltage having a magnitude proportional to the intensity of the skin damaging UVB radiation incident thereon. As the intensity of the UVB skin damaging radiation incident on detector 36 increases, the output voltage of the photodetector increases accordingly.

Printed circuit board 35 carries several components which enable microcomputer 31 to derive a digital signal having a magnitude related to the intensity of the skin damaging UVB radiation incident on photodetector 36 at the time U pushbutton 17 is activated or when T button 19 is activated after a certain operating sequence of buttons 16, 18 and 19. Variable resistor 38, which is preset at the time of manufacture for adjustment purposes of the photodetector, is one of the components mounted on printed circuit board 35. Resistor 38 and other components on printed circuit board 35 are connected to battery 26 and to terminals of microcomputer 31 by suitable connections, described infra.

Key switches associated with buttons 16-19 are connected to suitable inputs of microcomputer 31. The key switch associated with button 17 is illustrated; it is to be understood that the construction of the key switches associated with buttons 16, 18 and 19 is basically the same as that illustrated for the key switch associated with button 17. The key switch associated with button 17 includes dielectric stem 541, fixedly connected to bore 542 on the back face of button 17. Button 17 is free to translate, in response to tactile force, in well 543 on the side wall of case 10. At the end of dielectric post 541 is metal contact 544 which is normally biased by a spring (not shown) out of engagement with a stationary contact (not shown) connected to an input port of microcomputer 31. In response to tactile force being applied to button 17, post 541 and contact 544 are pushed to the right, as illustrated in FIG. 2, to provide a connection from one electrode of battery 26 to the stationary contact that is engaged by contact 544. Details of the contacts and springs associated with pushbutton 17 are not indicated, because such structures are well known to those of ordinary skill in the art.

Reference is now made to FIG. 3 of the drawings, a top view of LCD 33 that includes two back planes, BP1 and BP2, selectively energized in response to signals from microcomputer 31. LCD 33 includes top and bottom rows 41 and 42 of numeric indicators and center row 40 of alpha indicators. Top row 41 includes seven numeric indicators 51–57, all having the same height. Bottom row 42 includes a selectively energized "1" numeric indicator 61, three numeric indicators 62, 63 and 64, each having a height equal to that of numeric 61, and two smaller numeric indicators 65 and 66, having a height which is the same as the height of numeric indicators 51–57. Numeric indicators 51–57 are arranged in row 41 from left to right, as viewed in FIG. 3, while indicators 61–66 are arranged in row 42 from left to right, as illustrated in FIG. 3. Numeric indicators 51–57 are sometimes referred to herein as digits 6–12, respectively, while numeric indicators 63–66 are sometimes referred to as digits 4–1, respectively. Units digit 61 and numeric indicator 62 are referred to herein as digit 5. Row 40 includes symbol 75, consisting of a circle and eight radially directed arms, to resemble the sun, and alpha indicators 81–86 that read "SKIN", "SPF", "DATA", "RUN", "TMR", and "DATE".

LCD 33 also includes horizontal bar 71, between numerics 51 and 52, colon 72 between numerics 55 and 56, colon 73 between numerics 62 and 63 and the letter "P", to the left of units digit 61.

Each of numeric indicators 52–57 and 62–66 includes seven segments, together forming the digit 8 when all segments are activated during a complete cycle of microcomputer 31. The digit values, between 1 and 9, are selectively energized, in response to output signals of microcomputer 31. The shaded segments of numeric indicators 51–57 and 62–66 are selectively activated in response to back plane BP1 being energized. The remaining, unshaded segments of numeric indicators 51–57 and 62–66 are activated in response to back plane BP2 being energized. In addition, dash 71, colon 72, colon 73, P character 74 and sun character 75 are energized in response to back plane BP2 being energized. The energization frequency of back planes BP1 and BP2 is sufficiently fast to cause the human eye to perceive the constantly pulsating segments as being constantly illuminated.

Connections are established between output terminals of microcomputer 31 and one shaded and one unshaded segment of a single one of numeric indicators 51–57 and 62–66 in many instances. In addition, the symbols and characters of elements 71–75 and 81–86 are connected to shaded segments of numeric indicators 52, 64, 64, 63, 53, 51, 52, 54, 55, 56, and 57.

When microcomputer 31 is activated so it is in the timepiece mode, numeric indicators 54–57 and 62–66 are supplied with signals to indicate month of the year, day of the month, and hour of the day, to the nearest second, as are units indicator 61 and P symbol 74, and colons 72 and 73. Indicators 54 and 55 indicate the numeric designation of the month of the year, indicators 56 and 57 indicate the day of the month, symbol 74 indicates, when illuminated, that the time of day is after 12:00 noon, units indicator 61 and numeric indicator 62 indicate the hour of the day from hour 1 through hour 12, indicators 63 and 64 indicate the minute of the hour, and indicators 65 and 66 indicate the second of the minute. Indicators 61–66 are constantly energized, regardless of the operating mode of microcomputer 31, as are colons 72 and 73; P character 74 is energized one-half of the time to indicate "PM". Time of day is always displayed on timepiece 10 and month of the year and day of the month are selectively displayed.

Numeric indicator 51 is selectively energized to indicate subject skin type, with values ranging from 1 to 6. As the numeric value of the skin type increases, the maximum acceptable dosage which the skin type can receive without harm increases, such that skin type is related to dosage in microjoules per square centimeter as follows:

| Skin Type | Dosage |
|-----------|--------|
| 1 | 15,000 |
| 2 | 25,000 |
| 3 | 30,000 |
| 4 | 45,000 |
| 5 | 60,000 |
| 6 | 99,000 |

In instructions provided to the user of device 10, skin types 1–6 are respectively associated with the following nomenclature: extremely fair, very fair, fair, average, dark and very dark. Numeric indicator 51 is energized in response to the output of microcomputer 31 only when the skin type of the subject is being entered in response to activation of keys 16–19, as appropriate and described infra.

Numeric indicators 52 and 53 are selectively responsive to the output of microcomputer 31 to indicate either sun protection factor (SPF) of the subject skin or the intensity of the UVB radiation incident on photodetector 36, or a previously stored value of the intensity of the UVB radiation incident on the photodetector. Selection of which of the possible values to be indicated by numeric indicators 52 and 53 is in response to activation of appropriate ones of keys 16–19. If the subject has no lotion or gel to protect against the damaging effects of UVB radiation on his skin, the numeric value of 1 is automatically displayed on numeric indicator 53 at the time data concerned with the subject SPF are to be entered into the microcomputer.

Numeric indicators 54–57 are selectively activated in response to the output of microcomputer 31 to indicate, in hours and minutes, the initial maximum exposure time of the subject to the UVB radiation detected by photodetector 36 and the remaining safe exposure time of the subject to derive the numerics displayed on indicators 54–57. The initial maximum safe exposure time is calculated in response to the intensity of the radiation initially incident on photodetector 36, SPF and skin type in accordance with:

$$\text{exposure time in seconds} = \frac{(DOSE)(SPF)}{(UVB_t)} \qquad (1)$$

where:

DOSE = the dosage, in microjoules per square centimeter, for the skin type which has been set into the microcomputer, $UVB_t$ is the intensity, in microwatts per square centimeter, of the UVB radiation incident on photodetector 36 at the time the subject initially is exposed to the UVB source, and SPF is the number of the sun protection factor entered into the microcomputer for the subject skin.

The value of $UVB_t$ is calibrated so that 1 microwatt per square centimeter incident on photodetector 36 is converted to a count of 8 in microcomputer 31. The maximum UVB intensity of 12.37 microwatts per square centimeter equates to a count of 99. The value of $UVB_t$ is variable between 1 and 99.

Microcomputer 31, after calculating maximum exposure time in accordance with Equation (1), converts the calculated time, which is in seconds, into hours and minutes by dividing by 3600 to get hours and by using the residual to get minutes. The resultant conversion produces signals that drive numeric indicators 54–57.

After the maximum exposure time has been set into microcomputer 31 in response to the inputs of skin type, SPF and the reading of photodetector 36, subsequent signals derived by the photodetector are not accumulated in the microcomputer. Instead, a count down or decremented counter in microcomputer 31 is initially set to a count determined by the value calculated from Equation (1) and is started in response to the operator activating the keys in a predetermined sequence, described infra. This counter is decremented every minute by microcomputer 31, to represent the remaining exposure time of the skin of the subject to the skin damaging UVB radiation. When the elapsed time equals the initially set time, piezoelectric crystal 29 is activated for a 10 second interval to provide an aural indication to the subject that the maximum permissible time he can be exposed to UVB skin damaging radiation has expired.

If, during use, the subject is desirous of determining how much additional time he can be exposed to the UVB radiation, buttons 16–19 are activated in a predetermined sequence, causing the microcomputer to read the contents of the count down counter in microcomputer 31 to numeric indicators 54–57. If the user wants to know the initially computed exposure time, buttons 16–19 are activated in a different sequence, causing numeric indicators 54–57 to be responsive to a register in microcomputer 31 that stores the value, in hours and hundredths of hours, from Equation (1). Microcomputer 31 responds to this stored value to compute hours and minutes, the displayed quantity.

It is possible with the device of FIGS. 1–4 to update the reading of photodetector 36 from time to time and/or to update the SPF input. For example, if a subject initially goes to the beach at 9:00 a.m. and does not put on any skin protecting lotion or gel, but one hour thereafter believes that the intensity of the sun has increased and decides to put on sun protecting lotion or gel he may alter the indication he obtained at 9:00 a.m., based on the conditions at that time, to the conditions which existed at 10:00 a.m. In this example, assume that a person has skin type 2 and that photodetector 36, while pointed at the sun, caused a count of 26 to be stored in microcomputer 31 at 9:00 a.m. In response to these conditions, wherein SPF=1, the maximum exposure time is calculated, based on Equation (1), as $$\frac{8(25,000)(1)}{(26)(60)} = 128 \text{ minutes} = 2 \text{ hours } 8 \text{ minutes}$$

Thereby, numeric indicators 54–57 respectively read 0, 2, 0, 8. At 10:00 a.m., the same person again points detector 36 at the sun and obtains a reading causing microcomputer 31 to have a count of 40. The time setting is calculated by microcomputer 31 as $$\frac{8(25,000)(1)}{(40)(60)} = 83 \text{ minutes} = 1 \text{ hour } 23 \text{ minutes}$$

The 1 hour elapsed time is subtracted from the new maximum exposure time of 1 hour, 23 minutes to provide a new maximum exposure time of 23 minutes which is displayed on numeric indicators 54–57 as 00:23.

Next assume that at 10:00 a.m. the subject also decided to apply a lotion with an SPF of 8 with photodetector 36 reading a count of 40. This causes a new maximum exposure time setting to be calculated by microcomputer 31 as:

$$\frac{8(25,000)(8)}{(40)(60)} = 667 \text{ minutes} = 11 \text{ hours } 7 \text{ minutes}$$

However, the subject one hour previous exposure time is $$\frac{60}{128}, \text{ i.e., } 47\%, \text{ of the new maximum exposure time}$$

whereby the subject can, under the altered exposure condition, remain exposed to the UVB for:

$$\frac{(128-60)(667)}{(128)} = 354 \text{ minutes} = 5 \text{ hours, } 54 \text{ minutes}$$

Now assume that at 10:00 a.m. the subject decided to apply a lotion with an SPF of 8, without taking a new reading from photodetector 36, so that the previous photodetector reading of 26 is used. This causes the time setting calculated by microcomputer 31 to be:

$$\frac{8(25,000)(8)}{(26)(60)} = 1026 \text{ minutes} = 17 \text{ hours } 6 \text{ minutes}$$

The subject can, under the altered exposure conditions, remain exposed to the UVB for $$\frac{(128-60)(1026)}{(128)} = 544 \text{ minutes} = 9 \text{ hours } 4 \text{ minutes}$$

In general for a change in exposure conditions the new remaining exposure time, $T_{nc}$, is calculated by multiplying the one's complement of the ratio of the previous actual exposure time, $T_{ae}$, to the previous maximum exposure time, $T_{pm}$, by the newly computed maximum exposure time, $T_{nm}$, i.e.:

$$T_{nc} = T_{nm}\left(1 - \frac{T_{ae}}{T_{pm}}\right)$$

The one's complement of the ratio is derived by dividing the count in the count down counter of microcomputer 31 that indicates remaining exposure time by the previously computed maximum exposure time. The resulting quotient is multiplied in microcomputer 31 by the newly computed maximum exposure time to determine the new remaining exposure time.

Reference is now made to FIG. 4 of the drawings, wherein microcomputer 31 and connections thereof are illustrated, in combination with external circuitry which drives the microcomputer. Microcomputer 31, being an SM530 SHARP microcomputer, is a 4-bit single chip CMOS microcomputer with 2016 bytes of read only memory (ROM), 88 words of random access memory (RAM), a melody generator circuit and a 96-segment liquid crystal display driver circuit. Microcomputer 31 includes eight binary bit input ports, 58 binary bit output ports, a timer/counter including an on chip 15-stage divider with reset, 10 second counter and 0.01 second counter, driven by an ON chip crystal controlled oscillator having a frequency of 32.768 kiloHertz. In the standby mode, microcomputer 31 has a current consumption of 1.5 microamperes and is driven by the 1.5 volt DC voltage battery 26. Microcomputer 31 has an instruction cycle of 91.5 microseconds.

Microcomputer 31 also includes an analog comparator circuit driven by a signal at one input port of the microcomputer. In response to the voltage at the input port being below a reference voltage applied internally to the comparator by the microcomputer circuitry, the comparator derives a binary signal having a first level; in response to the voltage at the input port being above the reference level, the output of the comparator is at the second binary level. The comparator circuit is connected to external circuitry including photodetector 36. The time between a start pulse for a charging circuit connected to the comparator and photodetector 36 and the output of the comparator changing between binary states is measured by counter circuitry in microcomputer 31 to provide a count in the microcomputer directly proportional to the intensity of the UVB radiation incident on detector 36.

The ports of microcomputer 31 are numbered 1-80, starting in the lower left-hand corner along the bottom edge of the microcomputer, as illustrated in FIG. 4, and proceeding in sequence in a clockwise direction to port 80 at the lower left-hand corner, on the left edge, so that there are 20 pins or ports on the left and bottom edges, 21 pins on the top edge and 19 pins on the right edge. Ports 21-44 and 57-80 are assigned to drive digits of display 33 such that digits 1-6 and 7-11 of the display are respectively responsive to the signals at ports 41-44, 37-40, 33-36, 29-32, 25-28, 21-24, 77-80, 73-76, 69-72, 65-68, 61-64, and 57-60. The connections from ports 21-44 and 57-80 to the segments on display 33 have nomenclatures which are alike in FIGS. 3 and 4, so that, for example, lead 17 associated with port 24, FIG. 4, is connected to lead 17 on display 33. (The terminals of the display illustrated in FIG. 3 and the ports of the microcomputer illustrated in FIG. 4 are associated with the same numerals that the actual commercial devices have.) Thereby, the upper right segment of numeric indicator 51 is energized in response to a binary 1 level being applied to port 24 of microcomputer 31 while back plane BP1 is activated to the binary 1 state. Back plane BP1 is responsive to the signal derived by microcomputer 31 at port 56 thereof. "SKIN" characters 81 are activated in response to a binary 1 signal being applied to port 24 while back plane BP2 is activated to the binary 1 state in response to the output of pin 1 of microcomputer 31.

Ports 14, 15, 17, 18, 20, 45 and 55 are open circuited, while ports 10, 12 and 50 are tied together to ground. Port 49 is connected to the negative electrode of battery 26, the positive electrode of which is connected to ground. Ports 46 and 47 are connected across capacitor 91 and are connected to an internal circuit of microcomputer 31 which effectively functions as a voltage doubler to provide proper bias voltage to the ports which drive liquid crystal display 33. The voltage doubler in microcomputer 31 also is coupled to ground via port 48 and capacitor 92. Power supply port 49, in addition to being connected to the negative electrode of battery 26, is connected to one electrode of filter capacitor 93, the other electrode of which is grounded.

Ports 53 and 54 are connected to crystal 94, having a resonant frequency of 32.768 kiloHertz. The opposite electrodes of crystal 94 are connected to ground via fixed capacitor 95 and variable capacitor 96. Port 52, connected to automatic clear circuitry in microcomputer 31, is also connected to ground through capacitor 96.

Port 13 of microcomputer 31 is connected internally to the melody generator circuit. Port 13 drives piezoelectric crystal 29, which provides an aural signal to the user when the melody generator circuit is enabled. Crystal 29 is connected to the emitter collector path of NPN transistor 98, having an emitter connected to the negative terminal of battery 26. The collector of transistor 98 is connected to one electrode of crystal 29, the other electrode of which is grounded; crystal 29 is shunted by coil 99. In response to the melody generator circuit being enabled transistor 93 supplies AC current to piezoelectric crystal 29 to cause the derivation of an audio tone.

Port 19 of microcomputer 31 applies test voltages during manufacture of the device.

Switches 101-104, respectively associated with pushbuttons 16-19, selectively connect input ports 3-6 with output ports 7-9 and 11. In particular, switch 101, associated with U pushbutton 17, selectively connects output port 11 with input port 3; switch 102, associated with M pushbutton 16, selectively connects output port 8 with input port 4; switch 103, associated with S pushbutton 18, selectively connects output port 8 15 with input port 5; and switch 104, associated with T pushbutton 19, selectively connects output port 7 with input port 6.

Port 51 is connected to the input of the comparator of microcomputer 31 and to external circuitry which derives a signal to indicate the intensity of the UVB radiation incident on photodiode 36. Port 51 is connected to the cathode of photodiode 36, having an anode connected to terminal 111. The anode cathode path of photodiode 36 is shunted by resistor 112, having a sufficiently low value to lower the dark resistance of photodiode 36 necessary to obtain an adequate reading from the microcomputer when very low UVB levels are incident on the photodiode.

Terminal 111 is connected to one electrode of capacitor 113, having a second electrode connected to the negative electrode of battery 26. Capacitor 113 is shunted by the emitter collector path of NPN transistor 114, having a collector connected to terminal 111 and an emitter connected to the negative electrode of battery 26, as well as a base responsive to the binary signal at port 16 of microcomputer 31. Terminal 111 is connected to ground through variable resistor 38, connected in series with the parallel combination of resistors 115 and 116. Resistor 116 is selectively connected in circuit at the time of manufacture by either leaving jumper lead 117 in place, or by cutting the jumper lead, depending on the reading of digit indicators 54-57 in response to a prescribed UVB radiation intensity on photodiode 36.

It has been found through actual experimentation that photovoltaic photodiode 36, capacitor 113 and transistor 114 and the circuitry associated therewith cause a ramping voltage having a substantially constant slope to be applied to the comparator connected to input port 51 of microcomputer 31. The comparator responds to the ramping voltage so that the switching time of the comparator, from the time the ramp begins, is directly proportional to the intensity of the UVB radiation incident on photodiode 36 and the voltage generated by the photodiode. The voltage developed across photodiode 36 when the photodiode is responsive to UVB radiation is polarized so that the voltage at the anode of the photodiode is positive relative to the voltage at the cathode thereof. When transistor 114 is forward biased in response to the voltage at output port 16 of microprocessor 31, the transistor emitter collector path has very low impedance, whereby the voltage at terminal 111 has a value of $-1.5$ volts, causing capacitor 113 to be discharged.

The $-1.5$ volt level at terminal 111 and the voltage across photodiode 36, which is proportional to be intensity of the UVB radiation incident on the photodetector, cause the input voltage of the comparator connected to port 51 of microcomputer 31 to be more negative than the $-1.5$ volt level applied by battery 26 to power supply port 49 of microcomputer 31; the voltage at port 51 varies between $-1.5$ and $-1.8$ volts. It is against conventional thinking for the voltage at any input port of a CMOS integrated circuit structure to be beyond the voltage applied to the power supply terminals of the CMOS structure. In other words, it is against conventional thinking for the voltage at input port 51 of CMOS microcomputer 31 to have a magnitude greater than $-1.5$ volts. We have found, however, through actual experimentation, that no deleterious effects occur as a result of the voltage at port 51 having a magnitude greater than $-1.5$ volts, i.e., no adverse effects occur to microcomputer 31 because the voltage applied to port 51 is between $-1.5$ volts and about $-1.8$ volts.

When the device of FIGS. 1-4 is in a watch or time mode, and at all other times except when U button 17 is pressed or T button 19 is activated after a proper activation sequence of buttons 16, 18 and 19, output port 16 of microcomputer 31 is at a binary zero level, causing the emitter collector path of transistor 114 to be back biased. Thereby, a constant voltage, at ground level, is applied to the anode of photodiode 36 and a constant voltage is applied by the photodiode to input port 51 of microcomputer 31. However, during these times, the output level of the comparator which is responsive to the voltage at port 51 is not read out to the registers of the microcomputer so that operations and indications derived by the microcomputer are unresponsive to the UVB intensity incident on photodiode 36.

In response to activation of button 17 or the correct activation sequence of buttons 16, 18 and 19, microcomputer 31 applies a binary one level to output port 16 thereof, causing the emitter collector path of transistor 114 to switch from a high to a low impedance state, whereby terminal 111 quickly changes from a zero volt level to the $-1.5$ volt level at the emitter of transistor 114. The change in voltage at terminal 111 is coupled through photodiode 36 to port 51, causing a change in the binary level of the output of the comparator in microcomputer 31 responsive to the voltage at port 51. The change in the output level of the comparator is not detected by processing circuitry in microcomputer 31 because such circuitry is disabled one computer cycle after the binary one level was originally applied to port 16.

During the next computer cycle the binary level of the signal at output port 16 is changed by the program of microcomputer 31 from one to zero, so that terminal 111 is no longer held at the $-1.5$ voltage level of the emitter of transistor 114. The voltage at terminal 111 starts to increase gradually from $-1.5$ volts in response to the positive current flowing into capacitor 113 from photodiode 36 and from ground via resistors 38 and 115. The increase in the voltage at terminal 111 has a substantially constant slope, regardless of the intensity of the UVB radiation incident on photodiode 36. As the intensity of the UVB radiation incident on photodiode 36 increases, the voltage across the photodiode increases, so that the initial voltage at port 51 during each ramping cycle is accordingly decreased. The time required for the comparator in microcomputer 31 connected to port 51 to reach a trigger voltage, determined by the level of the voltage at the other, internal input terminal of the comparator, is increased.

In response to the voltage at port 51 reaching the comparator trigger level the state of the comparator output changes to cause the binary signal at port 16 to change from a zero to a one level to forward bias transistor 114. Forward biasing of transistor 114 causes the voltage at terminal 111 to change suddenly back to $-1.5$ volts and the input to the comparator connected to port 51 to drop below the threshold of the comparator internal input. The computer again changes state so that during the next cycle of microcomputer 31 a back bias is again applied via port 16 to the base of transistor 114. The cycle is repeated as long as button 17 is depressed or button 18 is activated after the correct operating sequence of buttons 16, 18 and 19 which enables the output of the comparator to be coupled to digital processing circuitry in microcomputer 31.

The time during which the emitter collector path of transistor 114 remains in a back biased state increases and decreases as the intensity of the UVB radiation incident on photodiode 36 increases and decreases. Concomitantly, the number of counts supplied by oscillator circuitry of microcomputer 31 to a register of the microcomputer 31 as a result of the comparator connected to port 51 having a binary zero output increases and decreases with increases and decreases of UVB incident on detector 36, to indicate the level of the UVB radiation incident on photodiode 36.

To provide a better understanding of the functioning of the comparator in microcomputer 31 connected to port 51, photodiode 36, capacitor 113, transistor 114 and the circuitry associated therewith reference is now made to FIGS. 5a–5i. The waveforms of FIG. 5 represent three different conditions for the intensity of the UVB radiation incident on photodiode 36. FIGS. 5a, 5b and 5c are respectively the voltage waveforms at port 16, terminal 111 and port 51 for zero UVB radiation being effectively incident on photodiode 36; FIGS. 5d, 5e and 5f are respectively the voltage waveforms at port 16, terminal 111 and port 51 for a low level of UVB radiation incident on photodiode 36; and FIGS. 5g, 5h and 5i are respectively the voltage waveforms at port 16, terminal 111 and port 51 for maximum intensity of UVB radiation incident on photodiode 36.

Initially consider waveforms 5a, 5b and 5c, for the voltages at the base of transistor 114, at terminal 111 and at port 51 for a UVB radiation level incident on photodiode 36 less than the threshold for the photodiode, i.e., a UVB radiation level on the photodiode that results in no current being generated by the photovoltaic action of the photodiode. In one preferred embodiment for photodiode 36, the threshold is 0.3 microwatts. Under these conditions, in response to the negative going, leading edge of the output of port 16 of microcomputer 31, the emitter collector path of transistor 114 is cut off as indicated by the short duration pulse of FIG. 5a. Because photodiode 36 is not producing photovoltaic current under these conditions, the voltage at terminal 111 does not change in response to the emitter collector path of transistor 114 becoming cut off, as indicated by FIG. 5b. The −1.5 volt level at terminal 111 is coupled through photodiode 36 to port 51 of microcomputer 31, so that port 51 remains at a level of −1.5 volts, as indicated by the waveform of FIG. 5c.

Under these circumstances the input to the external input of the comparator in the microcomputer connected to port 51 is above the internal threshold of the comparator, causing the binary level at output port 16 of the microcomputer to revert immediately to a binary one level, as indicated by the positive going trailing edge of the waveform of FIG. 5a. Thereby, the emitter collector path of transistor 114 again becomes a low impedance, so that any tendency for capacitor 113 to discharge through transistor 114 is overcome. Since there is no change in state of the output of the comparator of microcomputer 31 connected to port 51, the register in the microcomputer assigned to store the magnitude of the UVB radiation incident on photodiode 36 is not enabled to be responsive to the microcomputer clock oscillator and stores a count of zero.

Next, consider the situation for maximum UVB radiation incident on photodiode 36 by referring to the waveforms of FIGS. 5g, 5h and 5i. Under these circumstances, photodiode 36 supplies sufficient current to terminal 111 to cause the voltage across the photodiode to be 0.3 volts with the voltage at terminal 111 being 0.3 volts greater than the voltage at port 51 of microcomputer 31.

In response to the negative going leading edge of the waveform of FIG. 5g applied by microcomputer port 16 to the base of transistor 114, the transistor is cut off so that terminal 111 is no longer at −1.5 volts. Thereby, capacitor 113 begins to charge in response to the current supplied to it by photodiode 36 and, to a much lesser extent, by the current supplied to it from the positive electrode of battery 26 (at ground potential) flowing through resistor 38. The current flowing through capacitor 113 causes the voltage at terminal 111 to increase linearly, with a certain slope, as indicated by the waveform of FIG. 5h. The linear increase in the voltage at terminal 111 is coupled through photodiode 36 to input port 51, as indicated by the waveform of FIG. 5i, which has about the same slope as the waveform of FIG. 5h. Because of the 0.3 volt potential across photodiode 36, the base of the waveform of FIG. 5i is −1.8 volts, i.e., the ramp of FIG. 5i begins at a level of −1.8 volts.

For the maximum UVB radiation intensity incident on photodiode 36, the waveforms of FIGS. 5h and 5i increase linearly until the waveform of FIG. 5i reaches a threshold of the comparator in microcomputer 31 connected to port 51 of the microcomputer. For the maximum UVB condition, the threshold is reached when the voltage at port 51 attains a voltage of −0.6 volts, i.e., when the waveforms of FIGS. 5h and 5i have ramped upwardly through a voltage increase of 1.2 volts. In response to the threshold of the comparator connected to port 51 being reached, the comparator changes state, resulting in a binary one level being applied by output port 16 of microcomputer 31 to the base of transistor 114, as indicated by the trailing, positive going edge of the waveform of FIG. 5g. In response to the resulting forward bias applied to transistor 114, the −1.5 volt level at the emitter of transistor 114 is supplied to terminal 111, causing virtually immediate discharge of capacitor 113, as indicated by the negative going, trailing edge of the waveform of FIG. 5h. The 1.2 volt transition of waveform 5h from −0.3 volts to −1.5 volts is coupled through photodiode 36 to input port 51 of microcomputer 31 so that the voltage at the input of the comparator drops from −0.6 volts to −1.8 volts, as indicated by the negative going, trailing edge of waveform 5i.

Transistor 114 remains in the forward biased condition until the next operating cycle of microcomputer 31 when the negative going leading edge of the waveform of FIG. 5g again occurs. The previously described operations associated with FIGS. 5g, 5h and 5i are repeated continuously as long as U key button 17 is activated or there is a predetermined operating sequence of M key 16, S key 18 and T key 19. The duration of the negative portion of the waveform of FIG. 5g is monitored by the clock and register in microcomputer 31 during each operating cycle while U key 17 is activated or there is a predetermined operating sequence of M key 16, S key 18 and T key 19. For the maximum intensity situation designated by FIGS. 5g, 5h and 5i, the register stores a count of 99, which count is stored in the register after U key 17 has been deactivated, until the next activation of the U key or after the predetermined sequence of keys 16, 18 and 19, until the next sequence of these keys.

Now consider the situation for the intensity of the UVB radiation incident on photodiode 36 being above the threshold of the photodiode, but considerably less than the maximum intensity level associated with FIGS. 5g, 5h and 5i. The waveforms at output port 16 of microcomputer 31, terminal 111 and the microcomputer input port 51 for such a situation are illustrated in FIGS. 5d, 5e and 5f, wherein photodiode 36 has sufficient photovoltaic action to cause the voltage at terminal 111 to be 0.1 volt above the voltage at input port 51 of microcomputer 31.

Under these circumstances, in response to the leading, negative going edge of the pulse of the waveform of FIG. 5d, transistor 114 is back biased, so that the voltage at terminal 111 is no longer at −1.5 volts. Thereby, capacitor 113 begins to charge, causing the voltage at terminal 111 (the waveform of FIG. 5e) to increase linearly with about the same slope that the voltage at terminal 111 increased in response to the maximum radiation intensity condition. The voltage increase at terminal 111 is coupled through diode 36 to port 51 of microcomputer 31, causing the voltage at port 51 to increase linearly from −1.6 volts, as indicated by the waveform of FIG. 5f. In response to the voltage at input port 51 of microcomputer 31 increasing sufficiently, to a value of approximately −1.25 volts for this situation, the output voltage of the comparator connected to port 51 changes, causing the positive going leading edge of the waveform of FIG. 5d to be applied to the base of transistor 114 to forward bias the transistor. Thereby, the −1.5 volt level at the emitter of transistor 114 is again applied to terminal 111, causing derivation of a negative going voltage change of −0.4 volts, as illustrated by the waveform of FIG. 5e. The −0.4 volt change in the voltage at terminal 111 is coupled through diode 36, so that the voltage at input port 51 of microcomputer 31 drops from −1.25 volts to −1.65 volts, as indicated in FIG. 5f.

From the waveforms of FIGS. 5f and 5i and the previous discussion, the threshold of the comparator of microcomputer 31 differs for the maximum intensity situation of the waveforms of FIGS. 5g, 5h and 5i relative to the lower intensity waveform situation of FIGS. 5d, 5e and 5f. We are unable to explain why this change in threshold value has occurred, but believe that it may be related to the fact that the voltage applied to terminal 51 is beyond the voltage applied by battery 26 to the microcomputer. In any event, we have found through actual experimentation that the time from the negative going leading edges of the waveforms of FIGS. 5a, 5d and 5g to the time of the negative going, trailing edges of these waveforms is proportional to the intensity of the UVB radiation incident on photodiode 36.

Hence, for the situation indicated by the waveforms of FIGS. 5d, 5e and 5f, the register in microcomputer 31 which is assigned to store an indication of the intensity of the UVB radiation stores a count of 33 immediately after U key or button 17 has been released. The register is started in synchronism with the leading, negative going edge of the waveform of FIG. 5d and is driven by a clock source until the comparator connected to port 51 changes state in response to the voltage of FIG. 5f reaching the comparator threshold.

A flow chart of operations performed by a user of the device illustrated in FIGS. 1-4 to set time, subject skin type, subject SPF and UVB radiation incident on photodiode 36 in microcomputer 31 is illustrated in FIG. 6. The operations performed in FIG. 6 are in response to activation of pushbuttons 16-19 and the radiation incident on photodiode 36 at the time U button 17 is activated or in response to a proper activation sequence of buttons 16, 18 and 19.

Prior to any of the operations of FIG. 6 being performed, microcomputer 31 is initially set, by installation of battery 26, to a month reading of 12, a day reading of 31 and a time of day reading of 12:00:00. The skin type and sun protection factor are both initially set to 1 and the register which stores incident radiation is initially set to 00.

The first operation 120 performed by the user involves setting the timing functions of the device. Time is set in a relatively conventional manner in response to activation of buttons 18 and 19, as indicated by operating steps 121-124. In response to the first activation of S button 18, the correct month is set by pressing T button 19. Then, the correct day of the month is set after button 18 has been activated, by pressing T button 19. Then, the hour of the day is set after S button 18 has again been activated by pressing T button 19. Then, after S button 18 has again been pressed, the correct minute is set by pressing T button 19. If it is again desired to set the month, day of the month, hour or minute, S button 18 is again pressed and the sequence is repeated, as indicated by operations 122, 123, 124. After any one of operations 121-124 has been completed, it is possible to return to operation 120 by pressing M key 16.

Operations 121-124 are arranged so that activation of T key or button 19 has no effect on signals stored in microcomputer 31 unless the T key activation was immediately preceded by activation of S key 18. While operations 121-124 are being performed, the digits representing the month, date, hour and minute respectively blink. While the month, date, hour and minute numeric indicators are being set, signals representing time indications stored in the register microcomputer 31 are frozen.

When the device of FIGS. 1-4 is in operation 120, the intensity of the UVB radiation incident on photodiode 36 may be determined by activating U button 17 which causes the program to advance to operation 125. Operation 125 cannot be entered if U button 17 is pressed immediately after S button 18 or T button 19 was pressed.

The program is advanced from operation 120 to operation 130 by activating M button 16. From operation 130, skin type, SPF and the reading of the UVB intensity incident on photodiode 36 can be stored in registers of microcomputer 31 to calculate maximum exposure time of the subject to the UVB.

To enter skin type after the microcomputer has been advanced to operation 130, S button 18 is activated, which causes numeric indicator 51 to start blinking, as indicated by operation 131. The subject then enters his skin type as the appropriate numeric 1-6 by pressing T button 19. Numeric 1 is initially displayed, in blinking form, on numeric indicator 51. If the subject does not have extremely fair skin, T button 19 is pressed until the appropriate numeral at numeric indicator 51 is displayed.

After the appropriate skin type numeric value has been entered, the operator activates S key 18, causing the program to advance to operation 132, at which time numeric indicator 53 displays a blinking value of one. The operator then presses T button 19, to increment a register in microcomputer 31, until the desired numeric value for SPF is indicated on numeric indicators 52 and 53.

After operation 132 has been completed, S button 18 is again pressed, i.e., activated, causing the program to go to operation 133. During operation 133, T button 19 is pressed and photodiode 36 is pointed at the source of UVB radiation. The intensity of the radiation incident on photodiode 36 is converted into a digital count, as described, supra, and stored in an appropriate register of microcomputer 31 while T button 19 is activated. The count stored in the register is read out to numeric indicators 54 and 55 which read 00-99, depending on the intensity of the incident UVB radiation. The signal stored in the appropriate register of microcomputer 31 while button 19 is activated during operation 133 is combined in the arithmetic logic unit of the microcomputer with signals previously stored in the microcomputer to compute a new value of maximum exposure time, as discussed supra.

The new maximum exposure time is computed in response to release of button 19 being sensed at the end of operation 133. A digital signal representing the computed new maximum exposure time is stored in two registers of the microcomputer; one of the registers stores the new maximum exposure time and the other is decremented so it functions as a count down counter. The count down counter is decremented from a setting indicative of new maximum exposure time at a rate of once a minute by clock oscillator circuitry of the microcomputer. Microcomputer 31 is programmed to combine the readings of these two registers to perform calculations of the type described supra in connection with the value for $T_{nc}$.

After operation 133 has been completed, S button 18 can again be pressed, to return the operating sequence to skin type operation 131 and operations 132 and 133 can be repeated with sequential reactivation of button 18. Alternatively, after each of operations 131-133 has been completed, the program can be returned to operation 130 by activating M button 125. In operation 130, activation of U button 17 enables the intensity of the UVB radiation currently incident on photodiode 36 to be detected and displayed on numeric indicators 54 and 55.

After operation 130 has been completed, the sequence advances to operation 135 by activating M button 16. During operation 135, time is displayed on numeric indicators 61–66 and the UVB reading stored in microcomputer 31 during operation 133 is displayed on numeric indicators 52 and 53, simultaneously with display of remaining exposure time, in hours and minutes, on indicators 54–57.

With the program at operation 135, activation of S button 18 causes the program to advance to operation 136. During operation 136 a count down counter in microcomputer 31 for storing the amount of time the subject can safely remain exposed to UVB radiation changes from a disabled to an enabled state, and vice versa, depending on the previous state of the count down counter. In other words, pressing S button 18 while the program is in operation 135 causes the remaining exposure time displayed on numeric indicators 54–57 to be changed either from a count down state to a frozen state or from a frozen state to a count down state. Operation 136 is included because of the likelihood of the subject changing from a situation in which he is exposed to skin damaging UVB radiation to a condition in which such exposure does not occur. For example, if the subject is on a beach sunbathing and takes a break to eat lunch, the count down timer should be deactivated. To these ends, operation 135 is entered by pushing M button 16 twice, followed by activation of S button 18. When the subject resumes exposure to the UVB radiation, operation 135 is again accessed and S button 18 is again pressed to restart the count down counter.

It is also possible, from operation 135, to determine the instantaneous value of the UVB radiation incident on photodiode 36, by pressing U button 17 to advance the program to operation 137. In operation 137, the instantaneous reading of UVB radiation incident on photodiode 36 is read out to numeric indicators 52 and 53, to replace the stored reading of UVB previously appearing on these numeric indicators. The subject is thereby quickly provided with an indication as to whether the present intensity of UVB incident on photodiode 36 has changed materially from the UVB reading incident on the photodiode at the time the calculation was made for maximum remaining exposure time as a result of operation 133. Observation of such change during operation 137, in conjunction with operation 135, is highly advantageous because of the likelihood that operation 135 was entered when the subject resumed exposure to the UVB radiation, as discussed supra in conjunction with operation 136. If the subject notices an appreciable difference between the stored reading of UVB on numeric indicators 52 and 53 during operation 135 and the current reading which replaces the stored reading in response to activation of button 17, during operation 137, he should return to operation 133 by pressing M button 16 twice and then pressing S button 18 three times. This will enable a new value of UVB to be stored, resulting in calculation of a new remaining exposure time.

To monitor the operations of FIG. 6, microcomputer 31 includes a four bit or stage program register responsive to key buttons 16–19 and switches 101–104 associated therewith. The four bits of the program register indicates in which one of stages 120–125 and 130–137 the program of FIG. 6 resides.

Reference is now made to FIG. 7 of the drawing, a flow diagram of operations performed by microcomputer 31 in response to activation of buttons 16–19 and other operations. The first operation 201, wherein the various registers of microcomputer 31 are initialized, occurs in response to battery 26 being connected to the power supply terminals of the microcomputer. During operation 201, the microcomputer registers storing signals representing skin type, SPF, elapsed exposure time and remaining exposure time, are respectively set to digital values representing the numeric values 1, 1, 00:00, and 00:00. Simultaneously, the registers for storing digital signals representing the numeric values for month of the year, day of the month, hour of the day, minute of the hour and second of the minute are respectively set to 12, 31, 12, 00, 00, the program register is set to a state associated with operation 120, FIG. 6 and a one bit register representing a.m. and p.m. is set to a value representing p.m.

From initializing operation 201, the program advances to display time operation 202. In operation 202 signals in the registers for hour of the day, minute of the hour and second of the minute are supplied to numeric indicators 61–66 and a signal in the single bit register indicative of whether the current time is a.m. or p.m. is supplied to "P" character 74. Display time operation 202 is entered invariably during each operating cycle of microcomputer 31.

After display time operation 202 has been completed, the program advances to operation 203, during which the contents of the program register are read to determine if the subject has activated buttons 16–19 to cause the program to be at any of program operations 120, 130 or 135.

In response to the program register indicating that the program is in operation 120 while operation 203 is being performed, the signal stored in the registers for month of the year and day of the month are supplied to numeric indicators 54–57. In response to the program register indicating that the program is in step 125 while operation 203 is being executed, the register where the instantaneous value of UVB incident on photodiode 36 is read out to numeric indicators 52 and 53 simultaneously with month of the year and day of the month being read out to numeric indicators 54–57.

In response to the program register indicating that the program is in operation 130 while operation 203 is being executed the signals indicative of skin type, SPF, and initially computed maximum UVB exposure time are respectively supplied to numeric indicators 51, 52–53, and 54–57. If, however, the program register indicates that operation 134 is being executed, as occurs in response to U button 17 being activated while the program is in operation 130, the signal in the register responsive to the instantaneous UVB radiation incident on photodiode 36 is supplied to numeric indicators 52 and 53 in place of the initially computed maximum UVB.

In response to the program register indicating that the program is at operation 135, the signal in the register associated with intensity of UVB radiation incident on photodiode 36, as determined during operation 133, is supplied to numeric indicators 52 and 53. Simultaneously, the count in the remaining exposure time count down counter of microcomputer 31 is supplied to numeric indicators 54–57. In response to the program register indicating that the program is in operation 137, the count stored in the register of microcomputer 31 for the instantaneous UVB radiation incident on photodiode 36 is supplied to numeric indicators 52 and 53, instead of the UVB indication derived during operation 133.

The steps of microcomputer 31 associated with operations 120, 130 and 135, and the branches leading from them including operations 121–125, 131–134 and 136–137, (FIG. 6) are illustrated on FIG. 7 as operations 204 and 205, respectively labeled "DISPLAY ST, SPF, UV, TIMER" and "DISPLAY MONTH, DATE".

In response to the program of FIG. 6 being in any one of operations 121–124 or 131–133, as signalled by the program register, a one-bit register in microcomputer 31 is set to a binary 1 state to indicate that there are blinking digits on display 33. The digits blink during operations 121–124 and 131–133 to signal to the subject that the digits associated with each operation are subject to change by activating T button 19.

In response to operation 206 indicating that digits on display 33 are blinking, the program register contents are sampled to determine if the program is in a branch of operation 120 or 130. In response to a "YES" indication during operation 206 and the program being in a branch of operation 120, the program advances to operation 207, which indicates that the display is in the blinking watch mode associated with a branch of operation 120. In response to the decision of operation 206 indicating a "YES" answer and the program register indicating that a branch of operation 130 is being executed, the program advances to blinking programming mode step. While the program is in operation 207 or 208, the time display associated with numeric indicators 61–66 and "P" character 74 blink, as do numeric indicators 52–57, as indicated by operation 09. In response to operation 206 indicating a "YES" result leading to operation 208, indicia 61–66 and "P" character 74 blink, as do indicia 51–57, as indicated by operation 211. These steps are indicated in the flowchart of FIG. 7 by operations 211, 202 and 204.

Blinking is effectively provided by disabling the registers which are connected via the output ports of microcomputer 31 to input terminals of display 33. The outputs of microcomputer 31 are disabled for one-half second and enabled for one-half second under the control of operations 207, 208, 209 and 211.

The states of switches 101–104 associated with pushbuttons 16–19 are read during operation 213 which is entered from either of operations 207 or 208. If none of buttons 16–19 is activated, the program advances to operation 214, during which the presence of blinking digits is again tested, as described supra in connection with operation 206. If the digits of display 33 are not blinking, the program advances to "SLEEP" operation 215. In operation 215, only time of day, month of the year and day of the month signals are supplied to indicator 33 and a minimum current load of 1.5 microamperes is drawn by the microcomputer and display. The program stays in sleep operation 215 until one of buttons 16–19 is activated or in response to 10 seconds elapsing as described infra.

During sleep operation 215 all signals supplied to the indicators of display 33 are in a static condition, except the signal supplied to seconds indicator 66 which is continuously responsive to the output of a register that is driven by the clock oscillator to signal ten different one second increments. During sleep operation 215 the program operations of FIG. 7 are not executed. However, a register in microcomputer 31 is wired to be responsive to pulses that are derived by the microcomputer timing circuitry once every ten second and registers responsive to closure of switches 101–104 to enable sleep operation 215 to be exited once every ten seconds and in response to any of switches 101–104 being closed.

If operation 214 indicates that the digits of display 33 are blinking, the program returns to display time operation 202.

If operation 206 indicates that the digits of display 33 are not blinking, the program advances to operation 216. During operation 216 a register in microcomputer 31 that is driven by the clock oscillator of the computer is examined to determine if 10 seconds have elapsed since the last time the clock circuitry of microcomputer 31 derived a ten second pulse. If operation 216 indicates that the 10 second interval has elapsed, as indicated by a so called 10 second flag, the program advances to wake-up operation 219 which is also entered in response to closure of any switches 101–104. From operation 219, the program loops back to operation 216.

When operation 216 indicates that the 10 second flag is set, the register for time of day is incremented by 10 seconds during operation 217 and the register which stores a signal indicative of remaining exposure time is decremented during operation 218 by a count of one, to indicate a 10 second decrease in the remaining exposure time. If the remaining exposure time register is at a count of zero, the decrement input thereof has no affect on it. After operation 218 has been completed, the program returns to display time operation 202.

In response to the 10 second flag not being set, i.e., operation 216 deriving a "NO" response, the program advances to operation 213, during which the states of switches 101–104, associated with buttons 16–19, are read by sampling the states of four registers, each of which stores a signal indicative of the state of switches 101–104. If any of these registers is set to a binary one state to indicate that the button associated therewith is activated, the program advances to identify keys operation 220. From operation 220, the program advances to one of operations 221–234, respectively associated with M key 16 being activated, S key 18 being activated, T key 19 being activated and U key 17 being activated.

During operation 220, registers which are responsive to the signals coupled to input ports 3–6 of microcomputer 31 are sampled to determine which one of keys 16–19 is activated. In response to M key 16 being activated, the program advances to operation 221; in response to U key 17 being activated, the program advances operation 222; in response to S key 18 being activated, the program advances to operation 223; and in response to T key 19 being activated, the program advances to operation 224.

During operation 221 the initial determination is whether M key 16 went from a deactivated to an activated state during the previous operating cycle of microcomputer 31. In response to such a determination providing a "YES" response, the microcomputer program register is incremented by an appropriate count to indicate that one of operations 120, 130 or 135, FIG. 6, is being executed. The transition in the state of M key 16 also causes a signal to be supplied to the microcomputer melody generator circuit which is connected to terminal 13 to drive piezoelectric beeper crystal 29. In response to the register responsive to activation of M key 16 indicating that the M key remained in an activated state during the interval between adjacent cycle times of microcomputer 31, the program register remains static but the melody generator continues to drive terminal 13. These operations are indicated by step 227, FIG. 7. Upon completion of step 227, the program returns to operation 202.

In response to the program recognizing that U key 17 is activated, the program advances from operation 222 to operation 228. In operation 228, the program register contents are examined. If the program register indicates that any of operations 120, 130 or 135 is occurring while U key 17 is activated, the intensity of the UVB radiation incident on photodiode 36 is monitored and stored in a register of the microcomputer designated for this parameter. In particular, a forward bias voltage is applied via microcomputer terminal 16 to the base of transistor 114, followed by the application of a back bias voltage to the base of transistor 114. Simultaneously with the application of the back bias voltage to the base of transistor 114, a microcomputer counter responsive to the microcomputer oscillator is enabled. The counter is disabled when the ramping voltage associated with photodiode 36, capacitor 12, 113 and the comparator connected to terminal 51 reaches the comparator threshold.

These operations, described in detail supra with regard to FIGS. 4 and 5, are repeated continuously as long as button 17 is depressed, at a frequency that is an integral submultiple of the basic operating frequency of microcomputer 31. It is necessary to perform these operations at a frequency that is a submultiple of the basic operating frequency of microcomputer 31 because the interval associated with the maximum intensity of UVB radiation incident on photodiode 36 exceeds the basic operating cycle time of the microcomputer. However, once during each cycle time, the microcomputer program of FIG. 7, upon completing operation 228, returns to operation 202. Operation 202 is also reentered if U button 17 is activated simultaneously with the program register not being in a state associated with one of operations 120 or 130. The intensity monitoring function is not performed under the latter conditions, because those conditions indicate that the program is in one of operations 121-124, 131-133 all of which are associated with activating S pushbutton 18 and/or T pushbutton 19, exclusively of U pushbutton 17. If U button 17 is activated during or immediately after one of operations 121-124 or 131-133 without the intermediary of activating M button 16, an operator error has occurred. Such activity does not result in a reading of the intensity of the UVB radiation incident on photodiode 36.

During operation 228 the register of microcomputer 31 where the state of U button 17 is stored is sampled to determine if the U button was activated during the immediately preceding microcomputer cycle time. In response to such a determination being made, the melody generator circuit of microcomputer 31 connected to the microcomputer output terminal is activated, causing an aural beep to be applied to piezoelectric transducer 29.

In response to operation 223 being performed, as a result of S button 18 being activated, the program advances to operation 229. In operation 229, the initial step is to determine if S button 18 was activated during the preceding microcomputer cycle time. If the answer to such a determination is negative, the program returns to operation 202. If, however, S button 18 was activated during the preceding computer cycle time, the contents of the program register are sampled to determine if the program is residing in one of steps 120-124, 130-133 or 135. In response to the bits of the program register having values associated with one of states 120, 130 or 135, the program advances to operations 121, 131 or 136, respectively. In response to the program register having values associated with one of states 121-124 or 131-133 the program advances to the next state in the sequence, e.g., from state 121 to state 122 and from state 133 to state 131. During operation 229, a flag is set to signal that the display numeric indicators associated with operations 21-24 and 31-33, as appropriate, are to be activated. This flag, when combined with the bits of the program register enable and disable the signal supplied by the registers to the numeric indicia. The program then returns to operation 202.

In response to operation 224 being reached, as a result of key button 19 being activated, the program register of microcomputer 31 is sampled to determine if the program is in any of operations 121-124 or 131-133. If the program is not in one of operations 121-124 or 131-133, the program returns to operation 202. If, however, the program is in one of operations 121-124 or 131-132, a determination is made as to the one of these operations where the computer is residing and the register associated with that particular operation is enabled to receive pulses from the microcomputer clock oscillator. The registers are incremented at a rate that is perceptible to a human observer of the numeric indicators on display 33 once it has been determined that key button 19 has been continuously depressed for two seconds or more. Such a determination is made, in a conventional manner, by the microcomputer registers and clock circuitry. If it is determined that the program register is at a state associated with existing operation 133, the new value of maximum exposure time is calculated, the count down counter is set and the count up counter is enabled, as described supra in connection with FIG. 6. These operations are indicated by step 230. After the operations associated with step 230 have been completed, the program returns to step 202.

The preferred embodiment of the device disclosed herein achieves the objects set forth previously. In particular, the device is a timepiece having about the same cost as a conventional electronic sports watch, with the added feature of detecting the intensity of skin damaging UVB radiation and signalling to the user the expiration of maximum exposure time to such radiation in response to inputs of skin type and sun protection factor.

While there has been described and illustrated one specific embodiment of the invention, it will be clear that variations in the details of the embodiment specifically illustrated and described may be made without departing from the true spirit and scope of the invention as defined in the appended claims.

We claim:

1. Apparatus for indicating the amount of time skin of a subject can be safely exposed to skin damaging ultraviolet radiation comprising a detector for said radiation, means for deriving indications of subject skin type and sun protection factor on the subject skin, computer means responsive to said indications and an instantaneous value of said radiation incident on said detector for initially calculating the length of time the subject skin can be safely exposed to the radiation at a detected instantaneous value thereof, means responsive to said instantaneous detected value and independent of radiation accumulated on said detector for indicating when the length of time the subject skin can be safely exposed has expired, the indicating means being activated independently of accumulated radiation incident on the detector.

2. The apparatus of claim 1 wherein the computer means includes clock means and counter means initially set to the calculated length of time, the counter means and clock means being connected to each other and the indicator means so that the indicator means indicates when the calculated length of time has elapsed.

3. The apparatus of claim 1 further including means for modifying the calculated length of time the subject can be safely exposed to the radiation in response to an instantaneous value of said radiation incident on said detector as detected at a time subsequent to the time when the detector was previously responsive to the radiation.

4. The apparatus of claim 3 further including means for modifying the calculated length of time the subject can be safely exposed to the radiation in response to a change in the subject sun protection factor indication.

5. The apparatus of claim 1 further including means for modifying the calculated length of time the subject can be safely exposed to the radiation in response to a change in the subject sun protection factor indication.

6. The apparatus of claim 1 further including an analog comparator, a capacitor, and a switch, the analog comparator, capacitor and switch being connected to each other and to the detector so that the capacitor is charged by current flowing through the detector while the switch is open and the capacitor is discharged in response to the switch being closed, the comparator changing state in response to an input thereof exceeding a threshold level, a connection subsisting between the capacitor and the comparator input so the capacitor voltage affects the voltage level at said input, the state of the comparator controlling the opening and closing of the switch, the switch, capacitor, detector and comparator being connected so that the switch open time increases as the intensity of the UVB radiation incident on the detector increases and vice versa, the computer being responsive to the time the switch is open to derive the indication of the instantaneous value of UVB radiation.

7. A combined timepiece and suntan indicator device comprising a case having fastener means for enabling the case to be affixed to a human subject, the case including: a microcomputer, a digital indicator, plural key switches, a battery, window means, a photodetector behind the window means, the window means and photodetector having optical characteristics so that the photodetector derives a response indicative of skin damaging ultraviolet radiation incident on a subject wearing the device, the microcomputer including an oscillator and register means; the photodetector, microcomputer, key switches, indicator and battery being electrically connected to each other so that in response to activation of the key switches the register means stores signals indicative of time of day, intensity of the skin damaging ultraviolet radiation instantaneously incident on the photodetector at the time one of the key switches is activated, subject skin type, subject skin sun protection factor and elapsed time from the time one of said key switches is activated; and means for connecting the register means to the indicator so that the indicator displays digits indicative of time of day, the intensity of the skin damaging ultraviolet radiation instantaneously incident on the photodetector at the time said one key switch is activated, subject skin type, subject sun protection factor, and the remaining time the subject skin can be safely exposed to the skin damaging radiation from the time one of said key switches is activated independently of accumulated radiation incident on the photodetector.

8. The apparatus of claim 7 wherein the microcomputer includes an analog comparator, the device further including an electronic switch and a capacitor, the electronic switch, capacitor and photodetector being connected with each other so that the capacitor is charged by current flowing through the detector while the switch is open and the capacitor is discharged in response to the switch being closed; the comparator having an input for controlling the state of the comparator so that the comparator state changes in response to the voltage at the input exceeding a threshold, a connection between the capacitor and the input of the comparator so the capacitor voltage affects the voltage level at said input, and detector connected to each other, the state of the comparator controlling the opening and closing of the switch, the switch, capacitor, detector and comparator being connected so that the switch open time increases as the intensity of the UVB radiation incident on the detector increases and vice versa, the computer being responsive to the time the switch is open to derive the indication of the instantaneous value of UVB radiation.

9. The device of claim 7 wherein the key switches and microcomputer are connected for modifying the remaining length of time the subject can be safely exposed to the radiation in response to an instantaneous value of said radiation incident on said photodetector as detected at a time subsequent to the time when the photodetector was previously responsive to the radiation.

10. The device of claim 9 wherein the key switches and microcomputer are connected for modifying the remaining length of time the subject can be safely exposed to the radiation in response to a change in the subject sun protection factor indication.

11. The device of claim 7 wherein the key switches and microcomputer are connected for modifying the remaining length of time the subject can be safely exposed to the radiation in response to a change in the subject sun protection factor indication.

12. A method of signalling how long skin of a subject exposed to skin damaging ultraviolet radiation can safely remain exposed to said radiation comprising the steps of initially detecting the intensity of said radiation incident on the subject skin, responding to the initially detected intensity and indications of subject skin type and sun protection factor to derive an initial indication of how long the subject skin can be safely exposed to the radiation, activating a timer substantially simultaneously with the initial intensity detecting step to determine elapsed exposure time of the subject skin, and indicating the remaining time the subject skin can be safely exposed to the skin damaging ultraviolet radiation in response to the determined elapsed time and the initial indication independently of accumulated skin damaging ultraviolet radiation incident on the subject skin.

13. The method of claim 12 further including the step of detecting the intensity of said radiation incident on the subject subsequent to the initial detecting step to derive an indication of the intensity of said radiation at the time the radiation is subsequently detected, and modifying the remaining time indication in response to the indication of the intensity of said radiation at the time the radiation is subsequently detected independently of accumulated skin damaging ultraviolet radiation incident on the subject skin between the time the radiation is initially detected and the time the radiation is subsequently detected.

14. The method of claim 13 further including the step of activating an alarm in response to the remaining time being zero.

15. The method of claim 12 further including the step of activating an alarm in response to the remaining time being zero.

16. Apparatus for indicating the amount of time skin of a subject can be safely exposed to skin damaging ultraviolet radiation comprising a detector for said radiation, means for deriving indications of subject skin type and sun protection factor on the subject skin, computer means responsive to said indications and an instantaneous value of said radiation incident on said detector for initially calculating the length of time the subject skin can be safely exposed to the radiation at a detected instantaneous value thereof, means responsive to said instantaneous detected value for indicating when the length of time the subject skin can be safely exposed has expired, the indicating means being activated independently of accumulated radiation incident on the detector, means for modifying the calculated length of time the subject can be safely exposed to the radiation in response to an instantaneous value of said radiation incident on said detector as detected at a time subsequent to the time when the detector was previously responsive to the radiation, and means for modifying the calculated length of time the subject can be safely exposed to the radiation in response to a change in the subject sun protection factor indication.

17. Apparatus for indicating the amount of time skin of a subject can be safely exposed to skin damaging ultraviolet radiation comprising a detector for said radiation, means for deriving indications of subject skin type and sun protection factor on the subject skin, computer means responsive to said indications and an instantaneous value of said radiation incident on said detector for initially calculating the length of time the subject skin can be safely exposed to the radiation at a detected instantaneous value thereof, means responsive to said instantaneous detected value for indicating when the length of time the subject skin can be safely exposed has expired, the indicating means being activated independently of accumulated radiation incident on the detector, and means for modifying the calculated length of time the subject can be safely exposed to the radiation in response to a change in the subject sun protection factor indication.

* * * * *